United States Patent [19]

Lange et al.

[11] Patent Number: 4,769,062

[45] Date of Patent: Sep. 6, 1988

[54] THIAZOLYLAMIDES, THEIR PREPARATION, AND THEIR USE FOR CONTROLLING UNDESIRABLE PLANT GROWTH

[75] Inventors: Arno Lange, Bad Durkheim; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 820,232

[22] Filed: Jan. 21, 1986

[30] Foreign Application Priority Data

Feb. 5, 1985 [DE] Fed. Rep. of Germany ....... 3503773

[51] Int. Cl.$^4$ ................... C07D 277/46; A01N 43/78
[52] U.S. Cl. .......................... 71/90; 548/195
[58] Field of Search .................. 548/193; 71/90

[56] References Cited

U.S. PATENT DOCUMENTS

| | | | |
|---|---|---|---|
| 3,515,538 | 6/1970 | Kamakura et al. | 71/90 |
| 3,592,904 | 7/1971 | Evans | 514/310 |
| 3,775,425 | 11/1973 | Bosshard | 260/306.8 |
| 3,862,167 | 1/1975 | Ueno et al. | 260/306.8 |
| 4,021,224 | 5/1977 | Pallos | 71/88 |
| 4,225,610 | 9/1980 | Tarayre | 548/195 |
| 4,501,750 | 2/1985 | Sakano | 514/369 |

FOREIGN PATENT DOCUMENTS

| | | |
|---|---|---|
| 0001727 | 5/1979 | European Pat. Off. |
| 0006368 | 1/1980 | European Pat. Off. |
| 0069154 | 1/1983 | European Pat. Off. |

OTHER PUBLICATIONS

March, Advanced Organic Chemistry, p. 371 (1985).

Primary Examiner—Robert Gerstl
Attorney, Agent, or Firm—Keil & Weinkauf

[57] ABSTRACT

Thiazolylamides of the formula

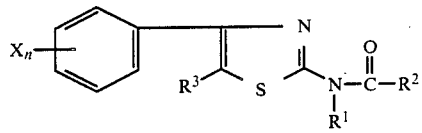

where $R^1$ if hydrogen or alkyl, $R^2$ is alkyl, alkenyl, alkynyl or cycloalkyl, $R^3$ is hydrogen, alkyl or halogen, X is halogen, alkoxy, haloalkoxy, alkyl, haloalkyl, cycloalkyl, alkylthio, nitro, cyano, unsubstituted or substituted phenyl or unsubstituted or substituted phenoxy, and n is 1, 2, 3 or 4, processes for their preparation, and their use for controlling undesirable plant growth.

6 Claims, No Drawings

THIAZOLYLAMIDES, THEIR PREPARATION, AND THEIR USE FOR CONTROLLING UNDESIRABLE PLANT GROWTH

The present invention relates to thiazolylamides, processes for their preparation, herbicides which contain these compounds as active ingredients, and methods for controlling undesirable plant growth with these compounds.

It is known that thiazolylamides which are unsubstituted or substituted in the heterocyclic moiety by halogen or alkyl possess herbicidal activity (German Laid-Open Application DOS No. 1,642,352).

Furthermore, some amides, such as acetamides or chloroacetamides, which carry unsubstituted or substituted alkyl radicals in the 4-position of the heterocyclic moiety are known to be intermediates or pharmaceutical substances.

We have found that thiazolylamides of the formula

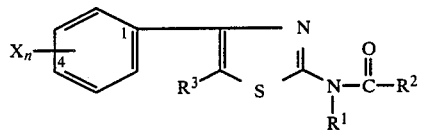
(Ia)

where $R^1$ is hydrogen or $C_1$–$C_4$-alkyl, $R^2$ is hydrogen or $C_3$–$C_7$-cycloalkyl or is $C_1$–$C_6$-alkyl, $C_2$–$C_6$-alkenyl or $C_2$–$C_6$-alkynyl, each of which is unsubstituted or substituted by halogen, by unsubstituted, halogen-substituted or $C_1$–$C_4$-alkyl-substituted phenoxy, by $C_1$–$C_4$-alkoxy or by $C_1$–$C_4$-alkylthio, $R^3$ is hydrogen, $C_1$–$C_4$-alkyl or halogen, X is hydrogen, halogen, $C_1$–$C_6$-alkoxy, $C_1$–$C_6$-haloalkoxy, $C_1$–$C_6$-alkyl, $C_1$–$C_6$-haloalkyl, $C_3$–$C_6$-cycloalkyl, $C_1$–$C_6$-alkylthio, nitro, cyano, benzyloxy, unsubstituted or halogen-substituted phenyl, or phenoxy which is unsubstituted or substituted by halogen and/or halomethyl, and n is 1, 2, 3 or 4, possess selective herbicidal activity.

In formula Ia, $R^1$ is hydrogen or $C_1$–$C_4$-alkyl, such as methyl, ethyl, n-propyl or isobutyl, preferably hydrogen, and $R^2$ is halogen or $C_3$–$C_7$-cycloalkyl or is $C_1$–$C_6$-alkyl, $C_2$–$C_6$-alkenyl or $C_2$–$C_6$-alkynyl, each of which is unsubstituted or substituted by halogen, by unsubstituted, halogen-substituted or $C_1$–$C_4$-alkyl-substituted phenoxy, by $C_1$–$C_4$-alkoxy or by $C_1$–$C_4$-alkylthio, eg. methyl, ethyl, n-propyl, isopropyl, tert.-butyl, vinyl, allyl, ethynyl, prop-1-ynyl, propargyl, but-2-ynyl, 1-methylprop-2-ynyl, but-4-ynyl, 1,1-dimethylprop-2-ynyl, cyclopropyl, cyclobutyl, cyclopentyl, cyclohexyl, methoxymethyl, ethoxymethyl, 2-methoxyethyl, 2-ethoxyethyl, methylthiomethyl, n-butoxymethyl, trichloromethyl, 1,2-dichloroethyl, 2,4-dichlorophenoxymethyl, 4-chlorophenoxymethyl, 2-methyl-4-chlorophenoxymethyl or 2,4,5-trichlorophenoxymethyl. $R^2$ is preferably $C_1$–$C_4$-alkyl, $C_2$–$C_4$-alkenyl or $C_2$–$C_4$-alkynyl, each of which is unsubstituted or substituted. Particularly preferred radicals $R^2$ are ethyl, cyclopropyl and isopropenyl. In formula Ia, X is hydrogen, halogen, $C_1$–$C_6$-alkoxy, preferably $C_1$–$C_4$-alkoxy, $C_1$–$C_6$-haloalkoxy, preferably $C_1$–$C_4$-haloalkoxy, particularly suitable halogen substituents being fluorine and/or chlorine, $C_1$–$C_6$-alkyl, preferably $C_1$–$C_4$-alkyl, $C_1$–$C_6$-haloalkyl, preferably $C_1$–$C_4$-haloalkyl, particularly suitable halogen-substituents being fluorine and/or chlorine, $C_1$–$C_6$-cycloalkyl, preferably $C_3$–$C_6$-cycloalkyl, $C_1$–$C_6$-alkylthio, preferably $C_1$–$C_4$-alkylthio, nitro, cyano or benzyloxy, or is phenyl which is unsubstituted or substituted by halogen, such as chlorine, or is phenoxy which is unsubstituted or substituted by halogen, such as chlorine, and/or halomethyl, such as trifluoromethyl, eg. fluorine, chlorine, bromine or iodine, preferably fluorine, chlorine or bromine, methoxy, ethoxy, difluoromethoxy, trifluoromethoxy, 3,3,3,2,1,1-hexafluoro-n-propoxy, 2,1,1-trifluoro-2-chloroethoxy, methyl, ethyl, tert.-butyl, trifluoromethyl, cyclohexyl, methylthio, ethylthio, nitro, cyano, benzyloxy, phenyl, 4-chlorophenyl, 4-trifluoromethylphenyl, 2-chloro-4-trifluoromethylphenoxy, phenoxy or 4-chlorophenoxy.

Preferred thiazolylamides of the formula Ia are those in which $R^1$ is hydrogen and $R^2$ is $C_1$–$C_4$-alkyl, preferably ethyl, $C_2$–$C_4$-alkenyl, preferably propenyl or isopropenyl, or $C_3$–$C_5$-cycloalkyl, preferably cyclopropyl. Other preferred thiazolylamides of the formula Ia are those in which X is $C_1$–$C_4$-haloalkoxy, in particular alkoxy which is substituted by fluorine and/or chlorine. Particularly preferred compounds are those in which $X_n$ is a $CHF_2O$ or $CF_3O$ group in the 4-position.

Amides of the formula

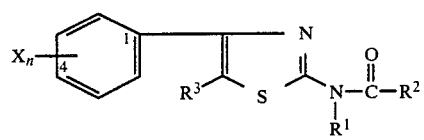
(I)

where $R^1$ is hydrogen or $C_1$–$C_4$-alkyl, $R^2$ is $C_2$–$C_4$-alkyl, $C_2$–$C_4$-alkenyl, $C_2$–$C_4$-alkynyl or $C_3$–$C_7$-cycloalkyl, $R^3$ is hydrogen, $C_1$–$C_4$-alkyl or halogen, X is halogen, $C_2$–$C_6$-alkoxy, $C_1$–$C_6$-haloalkoxy, $C_1$–$C_6$-alkyl, $C_1$–$C_6$-haloalkyl, $C_3$–$C_6$-cycloalkyl, $C_1$–$C_6$-alkylthio, nitro, cyano or unsubstituted or halogen-substituted phenyl or is phenoxy which is unsubstituted or substituted by halogen and/or halomethyl, and n is 1, 2, 3 or 4, are novel.

Thiazolylamides of the formula I can be prepared by a number of different conventional procedures. For example, in a process referred to below as method A, thiazolylamides of the formula I can be prepared by reacting a thiazolylamine of the formula

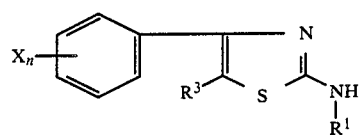
(II)

where $R^1$, $R^3$ and $X_n$ have the above meanings, with an anhydride of the formula

(III)

where $R^2$ has the above meanings, in the presence or absence of a catalyst, such as pyridine, and in the presence or absence of a solvent.

The thiazolylamides of the formula I may also be obtained by another process which is referred to below as method B, and in which a thiazolylamine of the formula II is reacted with a halide of the formula R²COHal    (IV)

where R² has the above meanings, and Hal is chlorine or bromine, preferably chlorine. The reaction is carried out in an inert solvent in the presence of an acid acceptor, such as an organic or inorganic base.

In another process C, an isocyanate of the formula V is reacted with a carboxylic acid according to the following equation:

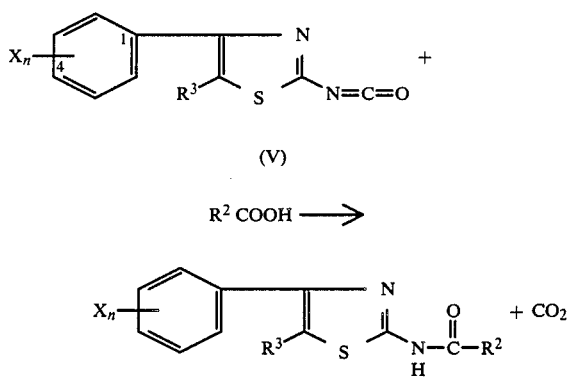

R² COOH ⟶ where R², R³ and $X_n$ have the above meanings. This synthesis route leads to thiazolylamides of the formula I in which R¹ is hydrogen.

Examples of typical reactants for reaction A are:
(a) 4-(4-Difluoromethoxyphenyl)-thiazol-1-ylamine with, for example, any of the following anhydrides: propionic anhydride, 2-methylpentanoic anhydride, cyclopropanecarboxylic anhydride, methacrylic anhydride or isobutyric anhydride.
(b) 4-(4-Trifluoromethoxyphenyl)thiazol-2-ylamine with one of the anhydrides stated in (a).

The reaction according to method A can be carried out in the presence or absence of an inert organic solvent, which may be a hydrocarbon, such as naphtha, benzene or toluene, an ether, such as dioxane, or a chlorohydrocarbon, such as chlorobenzene, carbon tetrachloride or perchloroethylene. Mixtures of these solvents may also be used. Instead of a solvent, the reaction can also be carried out in an excess of the anhydride of the formula III.

Suitable catalysts are tertiary amines, which are used in amounts of from 0.01 to 1.1 moles per mole of the thiazolylamine of the formula II. For example, picoline, pyridine, triethylamine, N-methylpiperidine and N,N-dimethylaniline can be used.

Although the anhydride of the formula III can be used as a solvent and the excess amount can be recovered for further use, it is generally most advantageous to use equimolar amounts of the reactants and to add a solvent.

The reaction temperatures can vary over a wide range, from about 0° C. to the boiling point of the solvent (about 150° C.).

The reactants used in method B are phenylthiazolylamines of the formula II and the acyl chlorides of the formula IV.

Typical reactants used in process B are:
(a) 4-(4-difluoromethoxyphenylthiazol-2-ylamines with one of the following acyl chlorides: acetyl chloride, propionyl chloride, isobutyryl chloride, methacrylyl chloride, 2-methylpentanoyl chloride, fluoroacetyl chloride or cyclopropanecarbonyl chloride.
(b) 4-(4-trifluoromethoxyphenylthiazol-2-ylamines with any of the acyl chlorides stated in a).

To carry out reaction B, the acyl halide is reacted in an excess of from 0 to 50 mol % per mole of II, in the presence or absence of a solvent and in the presence or absence of an acid acceptor, at from −20° to +150° C., preferably from 0° to +80° C., by a continuous or batchwise procedure (Houben-Weyl, Methoden der organischen Chemie, vol. VIII, page 655 et seq. (1951)).

Suitable acid acceptors are the conventional agents, for example alkali metal hydroxides, alkali metal carbonates, alkali metal alcoholates and tertiary organic bases. Specific examples of particularly suitable acid acceptors are sodium hydroxide, sodium bicarbonate, sodium methylate, sodium carbonate, the corresponding potassium salts, triethylamine, pyridine, trimethylamine, α- and β-picoline, lutidine, N,N-dimethylaniline, N,N-dimethylcyclohexylamine, quinoline, tri-n-propylamine, tri-n-butyl-amine and acridine, N,N-dimethylpiperazine, diethylpiperazine, methyl- and ethylpiperidine and methyl- and ethylpyrrolidine.

Reaction C is carried out by refluxing the reactants of the formula II and V in a high-boiling inert solvent, such as toluene, xylene, chlorobenzene or dichlorobenzene, until the evolution of carbon dioxide is complete.

In all versions of the process, the end products are isolated either (in the case of substances precipitated from the reaction mixture) by filtration under suction followed by purification by washing, recrystallization or chromatography, or by evaporation of the reaction mixture to dryness under reduced pressure and purification of the residue by recrystallization or chromatography.

Some of the substituted thiazolylamines of the formula II which are used as starting materials are novel. They can all be prepared by conventional processes (J. Chem. Soc. 67, 2242-3 (1945)).

The following thiazolylamines of the formula II are obtained:

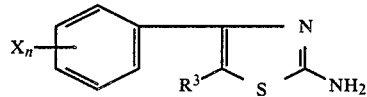

| $X_n$ | R³ | Mp. [°C.] |
|---|---|---|
| 4-CF₃ | H | 182–188 |
| H | CH₃ | 120–124 |
| 4-OCH₃ | H | 200–206 |
| 4-NO₂ | H | >300 |
| 4-CH₃ | H | 131–134 |
| 4-Cl | H | 163–166 |
| 3,4-Cl₂ | H | 160–164 |
| 2,4-Cl₂ | H | 161–163 |
| 2-Cl | H | 137–140 |
| 4-F | H | 109–114 |
| 2,4-F₂ | H | |
| 3-Br | H | 127–129 |
| 4-Br | H | 175–177 |
| 4-OC₂H₅ | H | 241–246 |
| 4-OCHF₂ | H | 113–118 |
| 4-OCF₃ | H | |
| 4-OC₆H₅ | H | 116–118 |
| 4-OCH₂—C₆H₅ | H | 155–159 |
| 3-Cl, 4-(4-chlorophenoxy) | H | 120–123 |
| 4-SCH₃ | H | 180–183 |
| 3-Cl, 4-OCH₃ | H | |
| 4-cyclo-C₆H₁₁ | H | 176–180 |
| 4-OCF₂—CHF—CF₃ | H | 95–98 |
| 2-OCH₃, 3,5-Cl₂ | H | |

-continued

| $X_n$ | $R^3$ | Mp. [°C.] |
| --- | --- | --- |
| 2,5-Cl$_2$ | H | 166–169 |
| 4-OCH$_3$ | CH$_3$ | 136–138 |
| 3-OCH$_3$ | H | 122–125 |
| 2,4-(OCH$_3$)$_2$ | H | 183–189 |
| 4-(4-CF$_3$, 2-Cl—C$_6$H$_3$) | H | |
| 4-Cl | CH$_3$ | 135–140 |
| 2,4-(OCHF$_2$)$_2$ | H | |
| 2-F | H | |
| 2,3,4-Cl$_3$ | H | |
| 2-OCHF$_2$, 4-CH$_3$ | H | |
| 2-OCHF$_2$, 4-Cl | H | |
| 2-Cl, 4-OCHF$_2$ | H | |
| 2-CH$_3$, 4-OCHF$_2$ | H | |

4-Aryl-2-amino-5-halothiazoles are obtained by the method described in J. Ind. Chem. Soc. vol. 36, No. 5 (1959).

EXAMPLE 1

106 g of 4-hydroxyacetophenone in 450 ml of dioxane are initially taken, and 156 g of NaOH in 390 ml of water and 4 g of tetrabutylammonium iodide are added. Gaseous chlorodifluoromethane is then passed in at 65°–70° C. in the course of 4.5 hours, until the mixture becomes saturated. Solid material is filtered off under suction and washed with dichloromethane, and the filtrate is extracted three times with dichloromethane. The dichloromethane phases are combined, washed with water, dried and evaporated down, and the residue is distilled to give 127.4 g of 4-difluoromethoxyacetophenone of boiling point 78°–81° C./0.1 mbar.

40 g of 4-difluoromethoxyacetophenone and 35.7 g of thiourea are initially taken and 61 g of iodine are added, the temperature increasing to 40° C. The mixture is then kept at 100° C. for 6 hours, water is added dropwise at this temperature, the mixture is left to cool to room temperature, and the product is filtered off under suction, washed with ether and dilute NH$_3$ solution, washed neutral with water and dried at 50° C. under reduced pressure. 33.8 g of 4-(4-difluoromethoxyphenyl)-thiazol-2-ylamine are obtained.

8.23 g of this product and 3.7 g of triethylamine in 80 ml of toluene are initially taken, 3.46 g of propionyl chloride are added dropwise, and the mixture is kept for 2 hours at 50° C. and overnight at room temperature. The solid material is filtered off under suction, washed thoroughly with water and dried overnight under reduced pressure at 50° C. 7 g of N-propionyl-[4-(4-difluoromethoxyphenyl)-thiazol-2-yl]-amine of melting point 186°–188° C. are obtained (compound No. 45).

EXAMPLE 2

33.5 g of thiourea are added to 30 g of 4-methoxyacetophenone, 56 g of iodine are added and the mixture is kept at 100° C. for 5 hours. The reaction mixture is discharged onto water, powdered, washed several times with ether then with ammonia solution and finally with water, and dried. 37.8 g of 4-(4-methoxyphenyl)-thiazol-2-yl-amine of melting point 194°–205° C. are obtained.

4.94 g of this product in 60 ml of toluene are initially taken together with 2.63 g of triethylamine. 6.23 g of 2,4-dichlorophenoxyacetyl chloride in 5 ml of toluene are added dropwise, and the reaction is allowed to proceed overnight at room temperature. The product is filtered off under suction, washed thoroughly with water and dried. 6 g of N-[4-(4-methoxyphenyl)-thiazol-2-yl]-(2,4-dichlorophenoxy)-acetamide of melting point 135°–139° C. are obtained (compound No. 4).

EXAMPLE 3

16.7 g of thiourea and 20 ml of methylchloroform are added to 18.6 g of 4-difluoromethoxyacetophenone: 14.9 g of sulfuryl chloride are added dropwise to the stirred slurry, the temperature increasing to 37° C. The mixture is heated to 80°–90° C. and kept at this temperature for 12 hours.

The product is filtered off under suction at room temperature, washed twice with methyl chloroform, twice with water, three times with dilute ammonia solution and then three times with water, sucked dry, and dried under reduced pressure at 40° C. 17.3 g (=71.5% yield) of 2-amino-4-(4-difluoromethoxyphenyl)-thiazoline of melting point 116°–120° C. are obtained.

9.7 g of 2-amino-(4-difluoromethoxyphenyl)-thiazoline in 80 ml of toluene are initially taken at room temperature, and 4.5 g of triethylamine are added. 4.6 g of cyclopropane carbonyl chloride are added dropwise, the temperature increasing from 22° C. to 42° C. Stirring is continued for a further hour at 45° C.

Thereafter, 150 ml of water are run in, and the solid material is filtered off under suction, washed twice with water and dried under reduced pressure. 8.8 g of N-cyclopropylcarbonyl-N-[4-(4-difluoromethoxyphenyl)-thiazol-2-yl]-amine of melting point 202°–203° C. are obtained.

The compounds below can be prepared by a similar method:

| Compound no. | $X_n$ | $R^3$ | $R^2$ | $R^1$ | M.p. [°C.] |
| --- | --- | --- | --- | --- | --- |
| 1 | 4-CF$_3$ | Cl | C$_2$H$_5$ | H | |
| 2 | 4-(4-trifluoromethyl-2-chlorophenoxy) | Cl | C$_2$H$_5$ | H | |
| 3 | H | CH$_3$ | C$_2$H$_5$ | H | 176–178 |
| 4 | 4-OCH$_3$ | H | 2,4-Cl$_2$—C$_6$H$_3$—O—CH$_2$— | H | 135–139 |
| 5 | 4-(4-trifluoromethyl-2-chlorophenoxy) | H | C$_2$H$_5$ | H | |
| 6 | 4-NO$_2$ | H | CH$_3$ | H | |
| 7 | 4-CF$_3$ | H | C$_2$H$_5$ | H | 219–224 |
| 8 | 4-CH$_3$ | H | C$_2$H$_5$ | H | 179–183 |
| 9 | 4-OCH$_3$ | H | C$_2$H$_5$ | H | 175–180 |
| 10 | 4-OCH$_3$ | H | cyclo-C$_3$H$_5$ | H | 165–180 |
| 11 | H | H | 2,4-Cl$_2$—C$_6$H$_3$—O—CH$_2$— | H | 140–142 |
| 12 | 4-CH$_3$ | H | n-C$_3$H$_7$ | H | |
| 13 | 4-Cl | H | C$_2$H$_5$ | H | 209–211 |
| 14 | 4-Cl | H | cyclo-C$_3$H$_5$ | H | 218–227 |
| 15 | 3-Cl | H | n-C$_4$H$_9$ | CH$_3$ | |
| 16 | 3,4-Cl$_2$ | H | C$_2$H$_5$ | H | 198–200 |
| 17 | 3,4-Cl$_2$ | H | CH$_3$O—CH$_2$ | H | |

-continued

| Compound no. | $X_n$ | $R^3$ | $R^2$ | $R^1$ | M.p. [°C.] |
|---|---|---|---|---|---|
| 18 | 4-F | H | $C_2H_5$ | H | 182–184 |
| 19 | 4-F | H | $2,4\text{-}Cl_2\text{--}C_6H_3\text{--}O\text{--}CH_2\text{--}$ | H | 168–173 |
| 20 | 4-F | H | cyclo-$C_3H_5$ | H | 201–208 |
| 21 | 3-Br | H | Cl—$CH_2$ | $C_2H_5$ | |
| 22 | 3-Br | H | $CH_3$ | $C_3H_7$ | |
| 23 | 3-Br | H | $CH_2=CH$— | H | |
| 24 | H | $CH_3$ | cyclo-$C_3H_5$ | H | |
| 25 | H | H | $CH_2=C(CH_3)$— | H | |
| 26 | H | Br | $C_2H_5$ | H | |
| 27 | 3-$OCH_3$ | H | $C_2H_5$ | H | |
| 28 | 3-$OCH_3$ | Cl | $C_2H_5$ | H | |
| 29 | 3-$OCH_3$ | Br | $C_2H_5$ | H | |
| 30 | 4-$OC_2H_5$ | H | $C_2H_5$ | H | |
| 31 | 4-$OC_2H_5$ | H | $C_2H_5$ | $CH_3$ | |
| 32 | 4-$OC_2H_5$ | H | Cl—$CH_2$— | H | |
| 33 | 4-$OCH_3$ | $CH_3$ | cyclo-$C_6H_{11}$ | H | |
| 34 | 4-$OCH_3$ | $CH_3$ | $CH\equiv C$— | H | |
| 35 | 4-$OCH_3$ | $CH_3$ | $CH_3$—S—$CH_2$ | H | |
| 36 | 4-$OC_6H_5$ | H | $C_2H_5$ | H | |
| 37 | 4-$OC_6H_5$ | H | $CH_2=C(CH_3)$— | H | |
| 38 | 4-$OC_6H_5$ | H | cyclo-$C_5H_9$ | H | |
| 39 | 4-$OCH_2C_6H_5$ | H | $C_2H_5$ | H | |
| 40 | 4-$OCH_2C_6H_5$ | Cl | $C_2H_5$ | H | |
| 41 | 4-$OCH_2C_6H_5$ | H | 2-Cl,4-$CH_3,C_6H_3$—$OCH_2$ | H | |
| 42 | 2-Cl | H | $2,4\text{-}Cl_2\text{--}C_6H_3\text{--}O\text{--}CH_2\text{--}$ | H | 160–162 |
| 43 | 2-Cl | H | $C_2H_5$ | H | 102–107 |
| 44 | 2-Cl | H | cyclo-$C_3H_5$ | H | 128–130 |
| 45 | 4-$OCHF_2$ | H | $C_2H_5$ | H | 186–188 |
| 46 | 4-$OCHF_2$ | H | $CH_2Cl$ | H | 126–128 |
| 47 | 4-$OCHF_2$ | H | cyclo-$C_3H_5$ | H | 202–203 |
| 48 | 3-Cl, 4-(4-chlorophenoxy) | H | $C_2H_5$ | H | 208–210 |
| 49 | 4-(4-chlorophenoxy) | H | $C_2H_5$ | H | |
| 50 | 3, 4-(4-chlorophenoxy) | H | Cl—$CH_2$— | H | |
| 51 | 4-$CH_3$ | H | Br—$CH_2$ | H | |
| 52 | 4-$SCH_3$ | H | $2,4\text{-}Cl_2\text{--}C_6H_3\text{--}O\text{--}CH_2\text{--}$ | H | 164–165 |
| 53 | 4-$SCH_3$ | H | $C_2H_5$ | H | 205–207 |
| 54 | 4-$SCH_3$ | H | $CH_2=C(CH_3)$— | H | |
| 55 | 3-Cl, 4-$OCH_3$ | H | $C_2H_5$ | H | 184–187 |
| 56 | 3-Cl, 4-$OCH_3$ | H | $CH_3$ | H | |
| 57 | 3-Cl, 4-$OCH_3$ | H | n-$C_3H_7$ | H | |
| 58 | 4-cyclo-$C_6H_{11}$ | H | $C_2H_5$ | H | 168–172 |
| 59 | 4-cyclo-$C_6H_{11}$ | H | cyclo-$C_3H_5$ | H | |
| 60 | 4-cyclo-$C_6H_{11}$ | H | $CH_3$—$CH=CH$— | $CH_3$ | |
| 61 | 4-O—$CF_2CHF$—$CF_3$ | H | $C_2H_5$ | H | 106–110 |
| 62 | 4-O—$CF_2CHF$—$CF_3$ | H | cyclo-$C_3H_5$ | H | |
| 63 | 4-O—$CF_2CHF$—$CF_3$ | Cl | $C_2H_5$ | H | |
| 64 | 4-O—$CF_2CHClF$ | H | $C_2H_5$ | H | |
| 65 | 4-O—$CF_2CHClF$ | Cl | $C_2H_5$ | H | |
| 66 | 4-O—$CF_2CHClF$ | Br | $C_2H_5$ | H | |
| 67 | 4-$OCF_3$ | H | $C_2H_5$ | H | 201–203 |
| 68 | 4-$OCF_3$ | Cl | $C_2H_5$ | H | |
| 69 | 4-$OCF_3$ | Br | $C_2H_5$ | H | |
| 70 | 4-$OCF_3$ | H | cyclo-$C_3H_5$ | H | 227–230 |
| 71 | 4-$OCF_3$ | H | $CH_2=C(CH_3)$— | H | |
| 72 | 4-$OCF_3$ | H | $C_3H_7(CH_3)_2C$— | H | |
| 73 | 4-$OCF_3$ | H | $C_3H_7$—$CH(CH_3)$— | H | |
| 74 | 4-$CF_3$ | H | $2,4\text{-}Cl_2\text{--}C_6H_3\text{--}O\text{--}CH_2\text{--}$ | H | 165–167 |
| 75 | 4-Cl | H | $C_2H_5$ | $CH_3$ | 140–143 |
| 76 | 4-$OCHF_2$ | Cl | $C_2H_5$ | H | |
| 77 | 4-$OCHF_2$ | Br | $C_2H_5$ | H | |
| 78 | 4-$OCHF_2$ | H | $2,4\text{-}Cl_2\text{--}C_6H_3\text{--}O\text{--}CH_2\text{--}$ | H | 140–143 |
| 79 | 4-$OCHF_2$ | H | $C_3H_7$—$C(CH_3)_2$— | | $n_D^{25}$ 1.5330 |
| 80 | 4-$OCHF_2$ | H | $C_3H_7$—$CH(CH_3)$— | H | 96–98 |
| 81 | 4-$OCHF_2$ | H | n-$C_3H_7$ | H | |
| 82 | 2,4-$Cl_2$ | H | $C_2H_5$ | H | 171–173 |
| 83 | 2,4-$Cl_2$ | H | cyclo-$C_3H_5$ | H | 217–220 |
| 84 | 2,5-$Cl_2$ | H | cyclo-$C_3H_5$ | H | 197–212 |
| 85 | 2,5-$Cl_2$ | H | $C_2H_5$ | H | 199–200 |
| 86 | 4-Br | H | $C_2H_5$ | H | 199–203 |
| 87 | 4-Br | H | cyclo-$C_3H_5$ | H | 233–235 |
| 88 | 2,4-$F_2$ | H | cyclo-$C_3H_5$ | H | 206–211 |
| 89 | 2,4-$F_2$ | H | $C_2H_5$ | H | 165–166 |
| 90 | 2,4-$(OCHF_2)_2$ | H | $C_2H_5$ | H | 100–105 |
| 91 | 2,4-$(OCHF_2)_2$ | H | cyclo-$C_3H_5$ | H | 148–150 |
| 92 | 2-F | H | cyclo-$C_3H_5$ | H | 165–167 |
| 93 | 2-F | H | $C_2H_5$ | H | 142–144 |
| 94 | 2,3,4-$Cl_3$ | H | $C_2H_5$ | H | 151–157 |
| 95 | 2,3,4-$Cl_3$ | H | cyclo-$C_3H_5$ | H | 187–190 |
| 96 | 2-$OCH_3$, 3,5-$Cl_2$ | H | cyclo-$C_3H_5$ | H | |
| 97 | 2-$OCH_3$, 3,5-$Cl_2$ | H | $C_2H_5$ | H | |

-continued

| Compound no. | $X_n$ | $R^3$ | $R^2$ | $R^1$ | M.p. [°C.] |
| --- | --- | --- | --- | --- | --- |
| 98 | 2-OCH$_3$, 4-CH$_3$ | H | C$_2$H$_5$ | H | |
| 99 | 2-OCH$_3$, 4-CH$_3$ | H | cyclo-C$_3$H$_5$ | H | |
| 100 | 4-OCH$_3$, 2-CH$_3$ | H | cyclo-C$_3$H$_5$ | H | |
| 101 | 4-OCH$_3$, 2-CH$_3$ | H | C$_2$H$_5$ | H | |
| 102 | 4-OCHF$_2$, 2-CH$_3$ | H | C$_2$H$_5$ | H | 137–138 |
| 103 | 4-OCHF$_2$, 2-CH$_3$ | H | cyclo-C$_3$H$_5$ | H | |
| 104 | 2-OCHF$_2$, 4-CH$_3$ | H | cyclo-C$_3$H$_5$ | H | |
| 105 | 2-OCHF$_2$, 4-CH$_3$ | H | C$_2$H$_5$ | H | 110–125 |
| 106 | 4-OCHF$_2$, 2-Cl | H | C$_2$H$_5$ | H | |
| 107 | 4-OCHF$_2$, 2-Cl | H | cyclo-C$_3$H$_5$ | H | |
| 108 | 4-Cl, 2-OCHF$_2$ | H | cyclo-C$_3$H$_5$ | H | 152–163 |
| 109 | 4-Cl, 2-OCHF$_2$ | H | C$_2$H$_5$ | H | 150–161 |
| 110 | 4-Cl, 2-OCH$_3$ | H | C$_2$H$_5$ | H | |
| 111 | 4-Cl, 2-OCH$_3$ | H | cyclo-C$_3$H$_5$ | H | |
| 112 | 2-Cl, 4-OCH$_3$ | H | cyclo-C$_3$H$_5$ | H | |
| 113 | 2-Cl, 4-OCH$_3$ | H | C$_2$H$_5$ | H | |
| 114 | 3,5-Cl$_2$ | H | C$_2$H$_5$ | H | |
| 115 | 3,5-Cl$_2$ | H | cyclo-C$_3$H$_5$ | H | |
| 116 | 2,6-Cl$_2$ | H | cyclo-C$_3$H$_5$ | H | |
| 117 | 2,6-Cl$_2$ | H | C$_2$H$_5$ | H | |
| 118 | 2,4-Cl$_2$ | Br | C$_2$H$_5$ | H | 151–153 |
| 119 | 4-t-C$_4$H$_9$ | H | C$_2$H$_5$ | H | 198–200 |
| 120 | 4-t-C$_4$H$_9$ | H | cyclo-C$_3$H$_5$ | H | 199–202 |
| 121 | 3-CF$_3$ | H | C$_2$H$_5$ | H | 157–160 |

The thiazolylamides of the formula Ia may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 18 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 26 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 10 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 12 is intimately mixed with 97 parts by weight of particulate kaolin. A dust is obtained containing 3% by weight of the active ingredient.

VII. 30 parts by weight of compound no. 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 3 is intimately mixed with 2 parts of the calcium salt of dodecylbenzenesulfonic acid, 8 parts of a fatty alcohol polyglycol ether, 2 parts of the sodium salt of a phenolsulfonic acid-ureaform-aldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.1 to 5 kg/ha, but is preferably from 0.25 to 3 kg/ha.

The action of the thiazolylamides of the formula Ia on plant growth is demonstrated in greenhouse experiments.

The vessels employed were plastic flowerpots having a volume of 300 cm$^3$, and which were filled with a sandy loam containing about 3.0% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.5 to 3 kg of active ingredient per hectare. No covers were placed on the vessels in this method.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Amaranthus spp., Arachis hypogaea, Avena sativa, Chenopodium album, Euphorbia geniculata, Glycine max, Ipomoea spp., Lamium amplexicaule, Lolium multiflorum, Mercurialis annua, Sinapis alba, Solanum nigrum,* and *Triticum aestivum.*

On preemergence application, for example compound no. 42 exhibited an appreciable herbicidal action on a grass species representative and a dicotyledonous plant used by way of example.

On postemergence application, compounds nos. 9, 13, 43 and 45 selected by way of example combatted broadleaved plants at a rate of 3.0 kg/ha. Unwanted broadleaved plants in crops such as groundnuts, soybeans and wheat were selectively controlled with a postemergence application of 0.5 kg/ha of compounds nos. 18 and 45.

Compounds nos. 47 and 80, applied postemergence at a rate of 1.0 kg/ha, are suitable for combatting a broad spectrum of unwanted plants in wheat without damaging the latter. The agents are selective.

Groundnuts, as an example of a broadleaved crop, were only insignificantly influenced by a postemergence application of 1.0 kg/ha of compound no. 61. A number of unwanted broadleaved plants can be combatted successfully.

Unwanted broadleaved plants, for example *Amaranthus retroflexus* and *Mercurialis annua,* can be combatted well in sunflowers on application of 1.0 kg/ha of compound no. 45. By contrast, Example 10 of German Laid-Open Application DE-OS No. 1,642,352 damages the crop plant considerably on postemergence application and has a much poorer herbicidal action.

Compound no. 45 is suitable for combatting Sesbania exaltata on postemergence application, without casuing any appreciable damage to the crop plant rice. By contrast, the compound of Example 10 of DE-OS No. 1,642,352 cannot be used for this purpose.

In view of the fact that the thiazolylamides of the formula Ia are well tolerated and can be applied by a variety of methods, they—or agents containing them—can be used not only in the crops used in the greenhouse experiments, but also in a further large number of crops for removing unwanted plant growth.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Veronica spp. | speedwell |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the thiazolylamides of the formula Ia may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds of the formula Ia, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A thiazolylamide of the formula

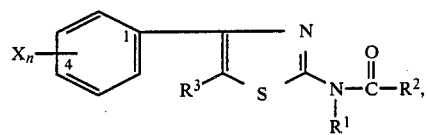

(I)

where $R^1$ is hydrogen or $C_1$–$C_4$-alkyl, $R^2$ is $C_1$–$C_6$-alkyl, $C_2$–$C_4$-alkenyl, $C_2$–$C_4$-alkynyl or $C_3$–$C_7$-cycloalkyl, $R^3$ is hydrogen, $C_1$–$C_4$-alkyl or halogen, X is $C_1$–$C_6$-haloalkoxy and n is 1, 2, 3 or 4.

2. A thiazolylamide of the formula I as set forth in claim 1, where $R^1$ is hydrogen and $R^2$ is $C_2$–$C_4$-alkyl, $C_2$–$C_4$-alkenyl or $C_3$–$C_5$-cycloalkyl.

3. A thiazolylamide of the formula I as set forth in claim 1, wherein $X_n$ is 4-$OCHF_2$.

4. A thiazolylamide of the formula I as set forth in claim 1, wherein $X_n$ is 4-$OCHF_2$, $R^1$ is H, $R^2$ is $C_2H_5$ and $R^3$ is H.

5. A thiazolylamide of the formula I as set forth in claim 1, wherein $X_n$ is 4-$OCHF_2$, $R^1$ is H, $R^2$ is $C_3H_7$—$CH(CH_3)$, and $R^3$ is H.

6. A process for controlling the growth of unwanted plants, wherein the unwanted plants or the areas to be kept free from unwanted plant growth are treated with a herbicidally effective amount of a thiazolylamide of the formula

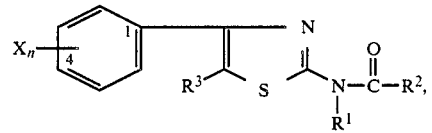

where $R^1$ is hydrogen or $C_1$–$C_4$-alkyl, $R^2$ is $C_2$–$C_4$-alkyl, $C_2$–$C_4$-alkenyl, $C_2$–$C_4$-alkynyl or $C_3$–$C_7$-cycloalkyl, $R^3$ is hydrogen, $C_1$–$C_4$-alkyl or halogen, X is halogen, $C_2$–$C_6$-alkoxy, $C_1$–$C_6$-haloalkoxy, $C_1$–$C_6$-alkyl, $C_1$–$C_6$-haloalkyl, $C_3$–$C_6$-cycloalkyl, $C_1$–$C_6$-alkylthio, nitro, cyano, unsubstituted or halogen-substituted phenyl, or phenoxy which is unsubstituted or substituted by halogen and/or halomethyl, and n is 1, 2, 3 or 4.

* * * * *